United States Patent [19]
Carson et al.

[11] Patent Number: 5,669,790
[45] Date of Patent: Sep. 23, 1997

[54] LEAD LUMEN SEALING DEVICE

[75] Inventors: Dean F. Carson; Richard J. Gable, both of Mountain View, Calif.

[73] Assignee: Ventritex, Inc., Sunnyvale, Calif.

[21] Appl. No.: 568,708

[22] Filed: Dec. 7, 1995

[51] Int. Cl.$^6$ .................................................. H01R 17/18
[52] U.S. Cl. ........................ 439/668; 439/271; 439/909; 439/948; 607/5; 607/37
[58] Field of Search .............................. 439/271, 909, 439/948, 668; 607/2, 5, 36, 37, 38

[56] References Cited

U.S. PATENT DOCUMENTS

| | | | |
|---|---|---|---|
| 3,394,341 | 7/1968 | Venn | 439/948 |
| 3,760,332 | 9/1973 | Berkovits et al. | 607/37 |
| 4,262,982 | 4/1981 | Kenny | 607/37 |
| 4,898,173 | 2/1990 | Daglow et al. | 607/37 |
| 4,906,210 | 3/1990 | McNiel | 439/863 |
| 4,922,927 | 5/1990 | Fine et al. | 607/37 |
| 5,534,019 | 7/1996 | Paspa | 607/38 |

*Primary Examiner*—Gary F. Paumen
*Assistant Examiner*—Tho Dac Ta
*Attorney, Agent, or Firm*—Steven M. Mitchell; M. Elizabeth Bush; Mark J. Meltzer

[57] ABSTRACT

A lead sealing device that resides within the connector cavity of a pacemaker or defibrillator intended to prevent fluid intrusion by automatically sealing the lead lumen when the lead connector is inserted. The sealing mechanism may be in the form of a silicone disk located at the base of the space defined by the connector cavity in which the lead is inserted to make electrical and physical contact. It may be fixedly located at the bottom of the connector cavity, or may be a movable plug located within the connector cavity at a location other than the bottom of the cavity, such as adjacent to the connector block. In that case, the pin will make contact with the movable plug immediately after passing through the connector block, and will remain in contact with and seal the lead lumen while the pin and plug are further advanced to bring the pin into its final location to make electrical contact with the connector contact.

8 Claims, 8 Drawing Sheets

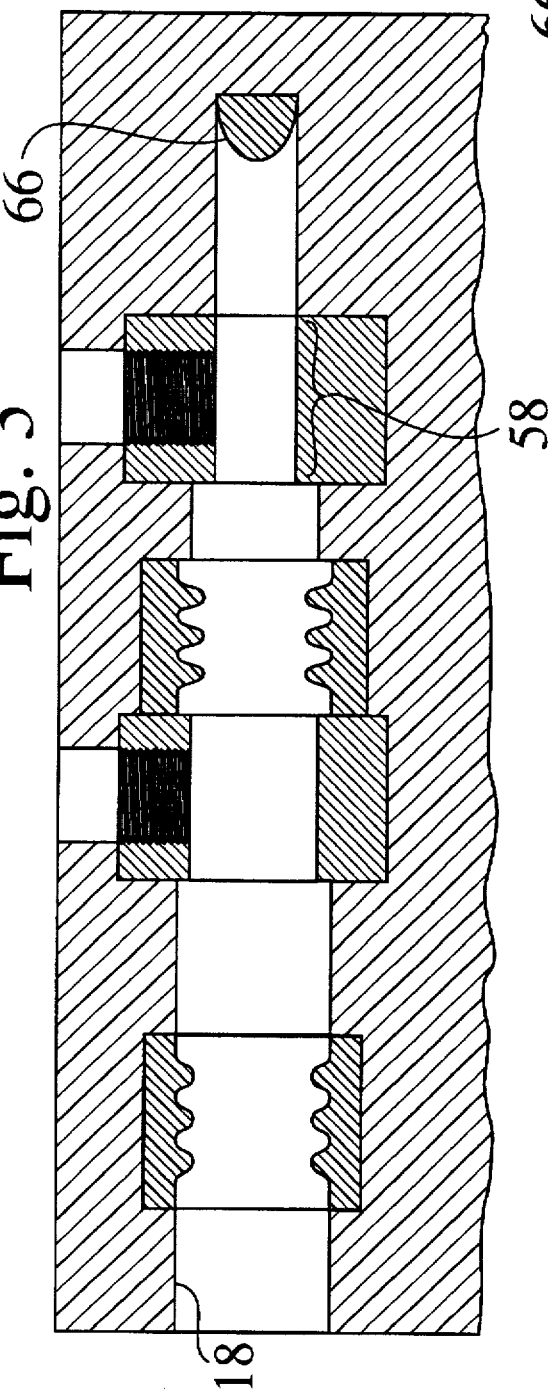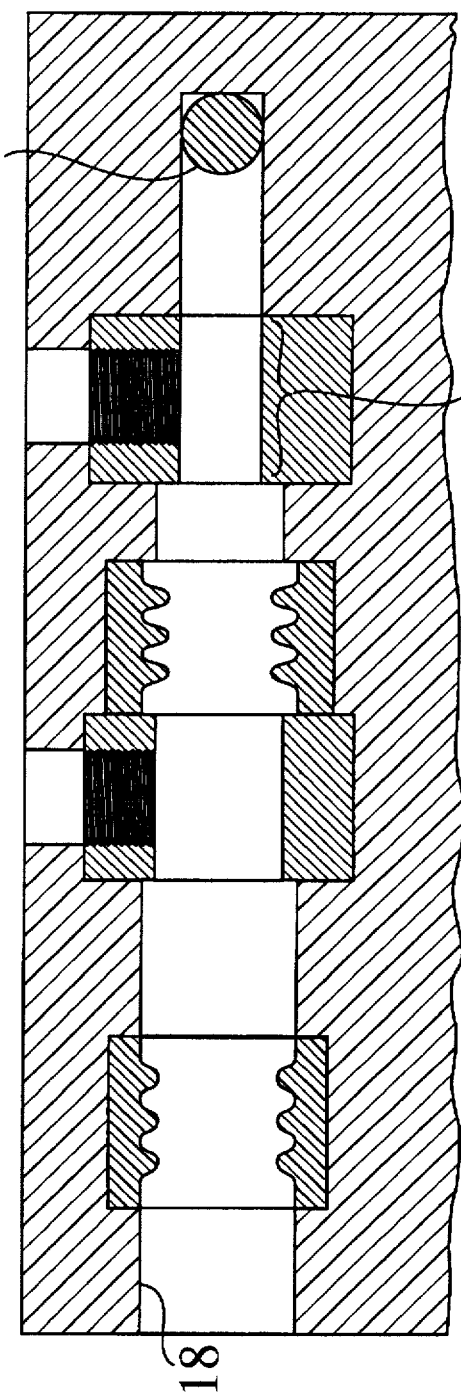

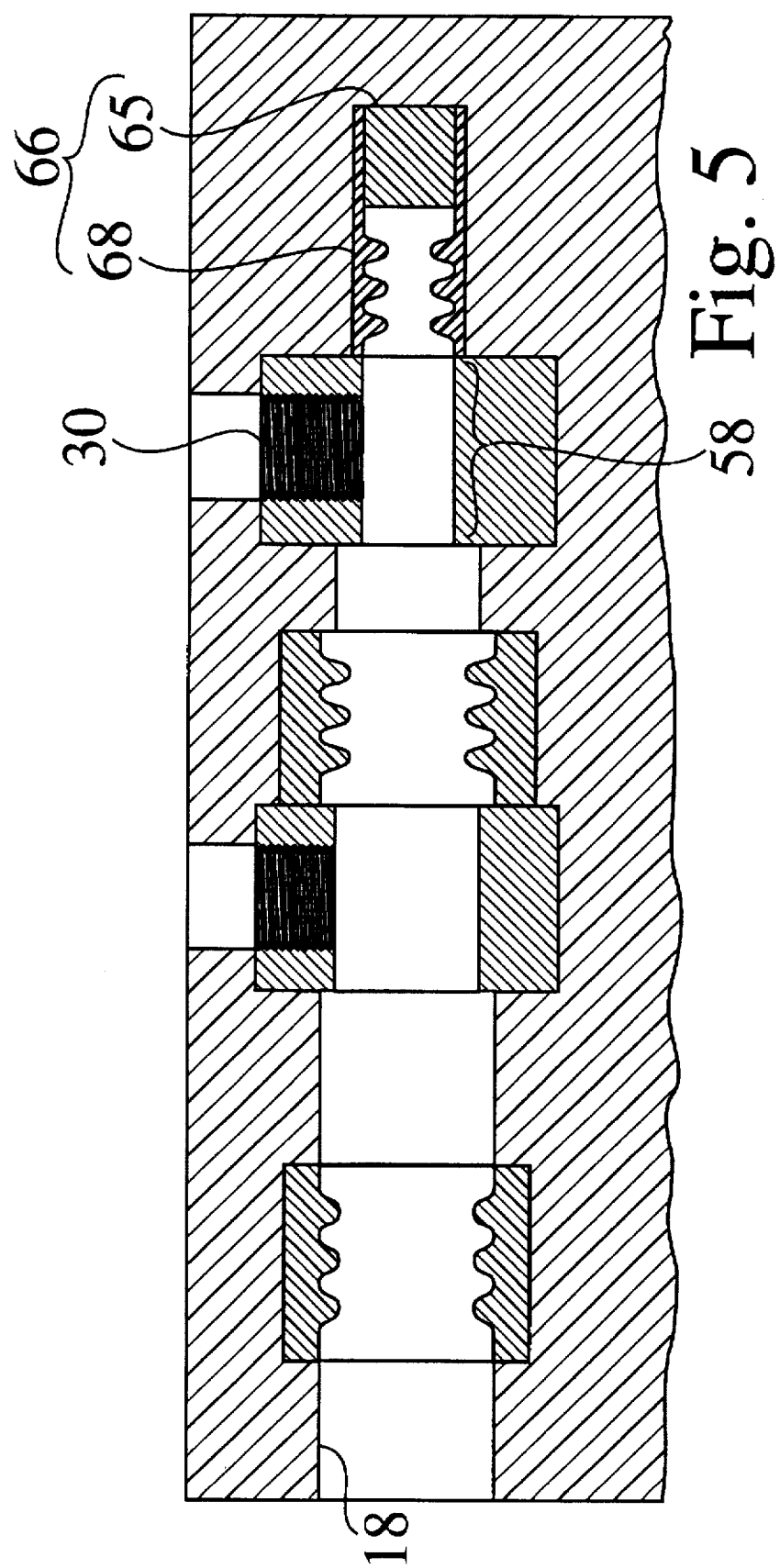

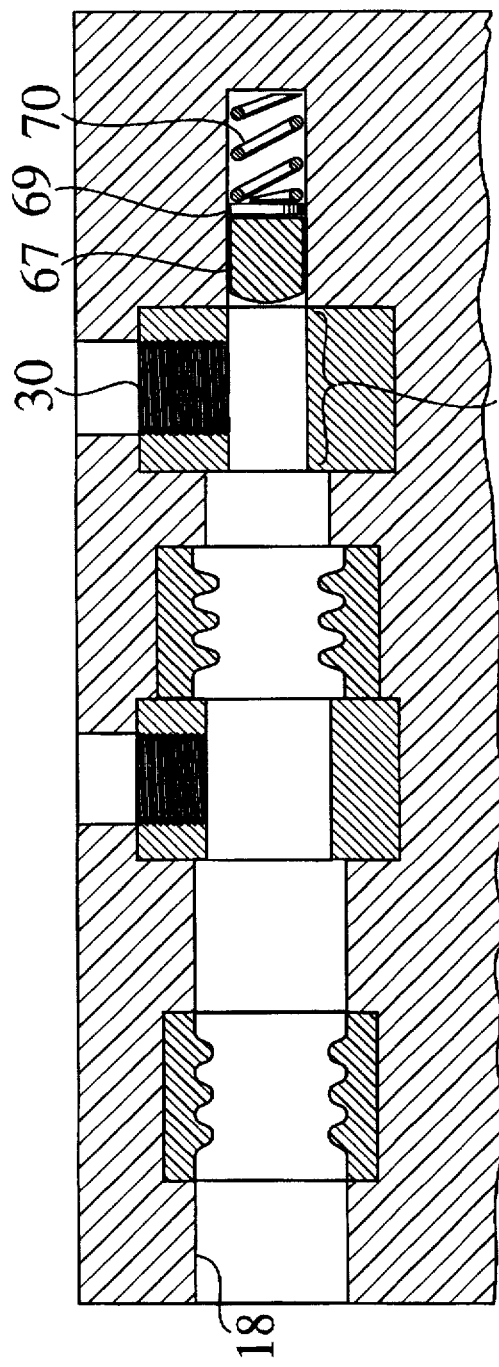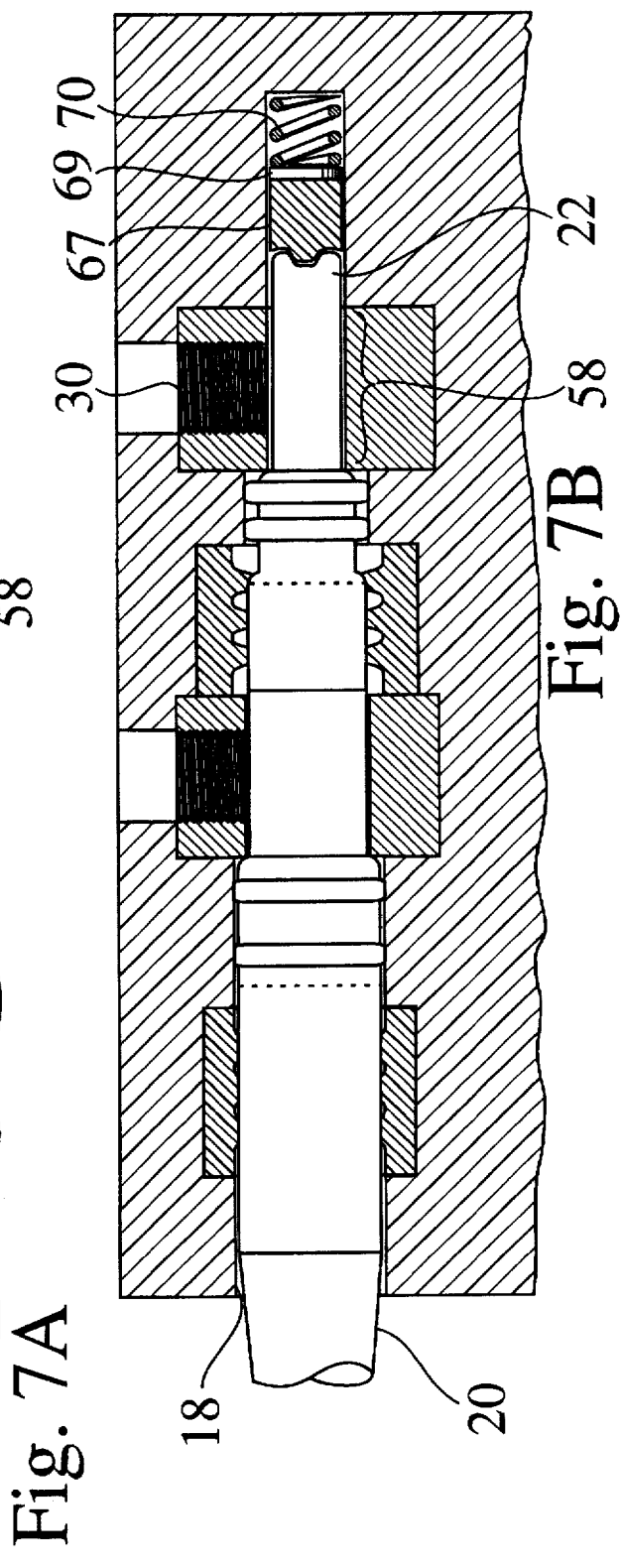

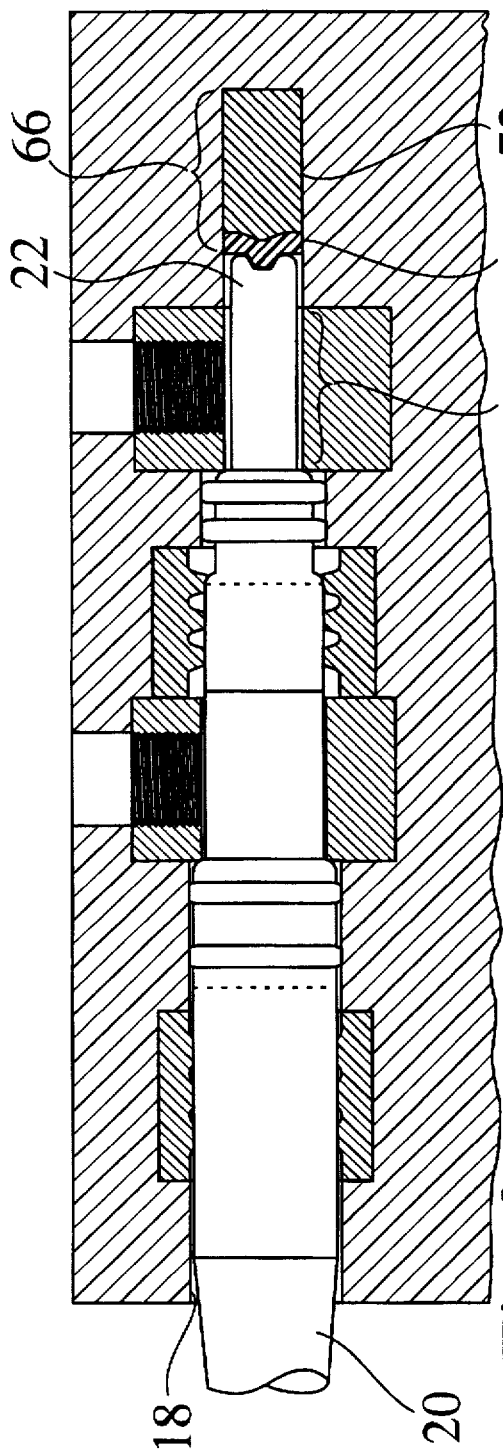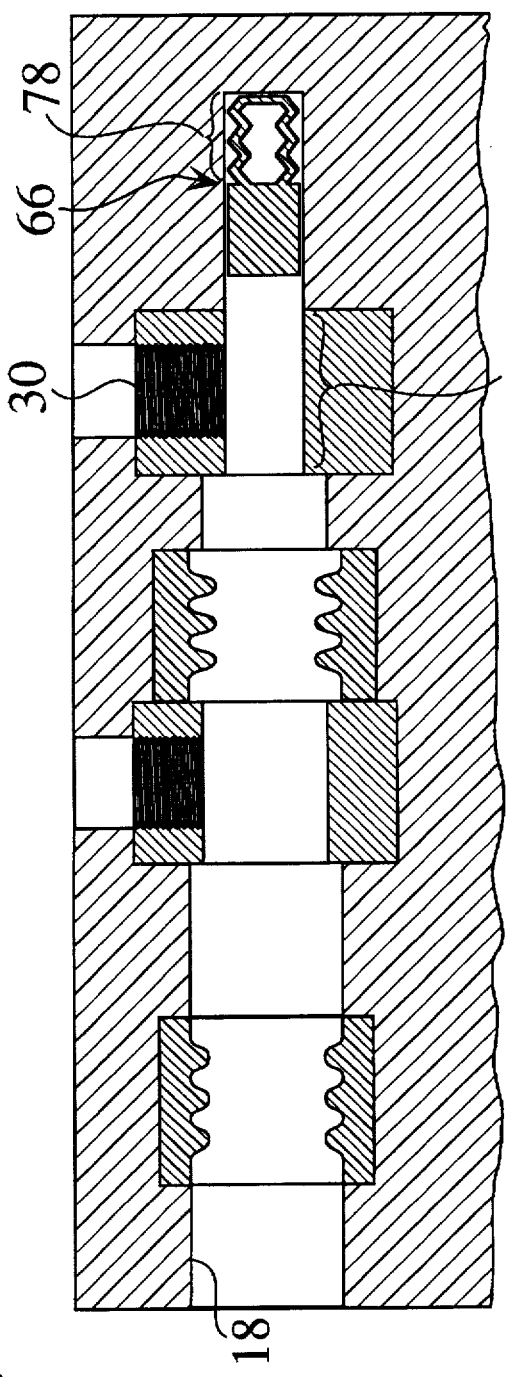

LEAD LUMEN SEALING DEVICE

FIELD OF THE INVENTION

The present invention relates generally to implantable devices, and more specifically to a seal for preventing fluid ingress into a lumen of an implanted lead.

BACKGROUND OF THE INVENTION

For pacemakers, defibrillators, and other devices that employ a lead having a lumen, leakage into the lead lumen can occur. Fluid within the lumen of a lead can prevent insertion of a lead extraction tool or a stylet for repositioning. Typical problematic fluids include normal body fluids such as blood or its components, infection-caused fluids, or irrigating fluids used during surgery such as sterile saline for flushing the tissue pocket in which the device will reside. This is especially a problem if the fluid is cellular in nature (e.g. blood) and clots or dries and leaves a residue of solid matter that is difficult to dissolve and can irreversibly clog the lumen.

Some of the pathways through which fluid may enter a pacemaker or defibrillator connector cavity, and then make its way into the lumen, are through the interfacial bond between the device and the header containing the connector cavities, between the lead connector sealing rings and the connector cavity, through the setscrew access in the header, or through a crack in the header. Hief et al. report, in "Cardioverter Discharges Following Sensing of Electrical Artifact Due to Fluid Penetration in the Connector Port," PACE, 18:1589–1591, that fluid penetration in the connector cavity of a defibrillator generator was caused by scratches on the lead sealing rings, which were possibly the result of the surgical procedure. Failure of the lead sealing rings led to electrical signals interpreted as ventricular fibrillation by the device, which triggered shock delivery. Because of the damaged sealing rings, lead replacement was required. The article did not mention whether there was any difficulty extracting the lead; however, this illustrates how fluid may enter a connector cavity, which could lead to clogging of the lead lumen, which would make lead extraction difficult if it becomes impossible to insert a lead extraction tool into the lead lumen.

Additional discussion of fluid intrusion can be found in an abstract by Forney et al., entitled "Fluid Intrusion into Pacemaker Headers: A Comparison," PACE, 18:867, April 1995. Explanted devices from several manufacturers were examined for the presence of blood and/or other fluid. Fluid intrusion was quantified using an ordinal ranking scale of 0–4 for visual score (0=no fluid; 4=saturated intrusion). Scores (mean±S.D.) for the seven manufacturers included in the study ranged from 0.7±1.0 to 2.2±1.2. This illustrates that at least partial fluid intrusion is a common occurrence.

It is therefore an object of the invention to provide a connector assembly for an implantable device which prevents or reduces the likelihood of fluid intrusion in a lead lumen.

SUMMARY OF THE INVENTION

The invention comprises a gasket mechanism that resides within the connector cavity of an implanted pulse generator and is intended to prevent fluid intrusion into a lumen of a lead plugged into the connector cavity by automatically sealing the lead lumen when the lead connector is inserted. As used herein, the term "connector cavity" refers to a connector cavity within the header of or adaptor for a pacemaker, defibrillator, or other implantable stimulator or recording device, into which a lead connector can be inserted. In a preferred embodiment of the invention, a disk is located at the base of a space defined by the connector cavity in which the lead is inserted to make electrical and physical contact.

The lead typically has a metal lead connector pin extending from the proximal end of the lead. This connector pin may be hollow so as to allow the passage of a stylet to facilitate insertion and positioning. After placement, the styler is removed, and the lead connector is inserted into the connector cavity causing the tip of the lead connector pin to make contact with the silicone gasket. This contact occurs after the pin is inserted past the connector contact, which may be a connector block that contains a setscrew to mechanically and electrically couple the lead connector pin to the connector cavity of the pulse generator. The gasket is made of a material which is soft enough to compress approximately 5 to 20% to seal the lumen of the lead connector pin from fluid intrusion.

The gasket may be fixedly located at the bottom of the connector cavity. Alternatively, the gasket may be a movable plug located within the connector cavity at a location other than the bottom of the cavity, such as adjacent to the connector block. In that case, the pin will make contact with the movable plug immediately after passing through the connector block, and will remain in contact with and seal the pin lumen while the pin and plug are further advanced to bring the pin into location to make electrical contact with the connector block. The friction required of the plug on the header wall to prevent its movement after implant and allow for acceptable compression of the gasket material for adequate sealing will be virtually unnoticeable by the physician during insertion of the pin and pushing of the plug.

BRIEF DESCRIPTION OF THE DRAWINGS

The various features and advantages of the present invention may be more readily understood with reference to the following detailed description taken in conjunction with the accompanying drawings in which:

FIG. 3 illustrates another embodiment of the lumen sealing device having a disk shape with a curved sealing surface;

FIG. 4 illustrates another embodiment of the lumen sealing device having a spherical shape;

FIG. 5 illustrates another embodiment of the lumen sealing device having a combination of an end disk and circumferential seals;

FIGS. 7A and 7B illustrate yet another embodiment of the lumen sealing device in the form of a pushable plug having a spring;

FIG. 8 illustrates another embodiment of a composite lumen sealing device;

FIG. 9 illustrates still another embodiment of a lumen sealing device having a bellows portion.

DETAILED DESCRIPTION OF THE INVENTION

Figure 1:
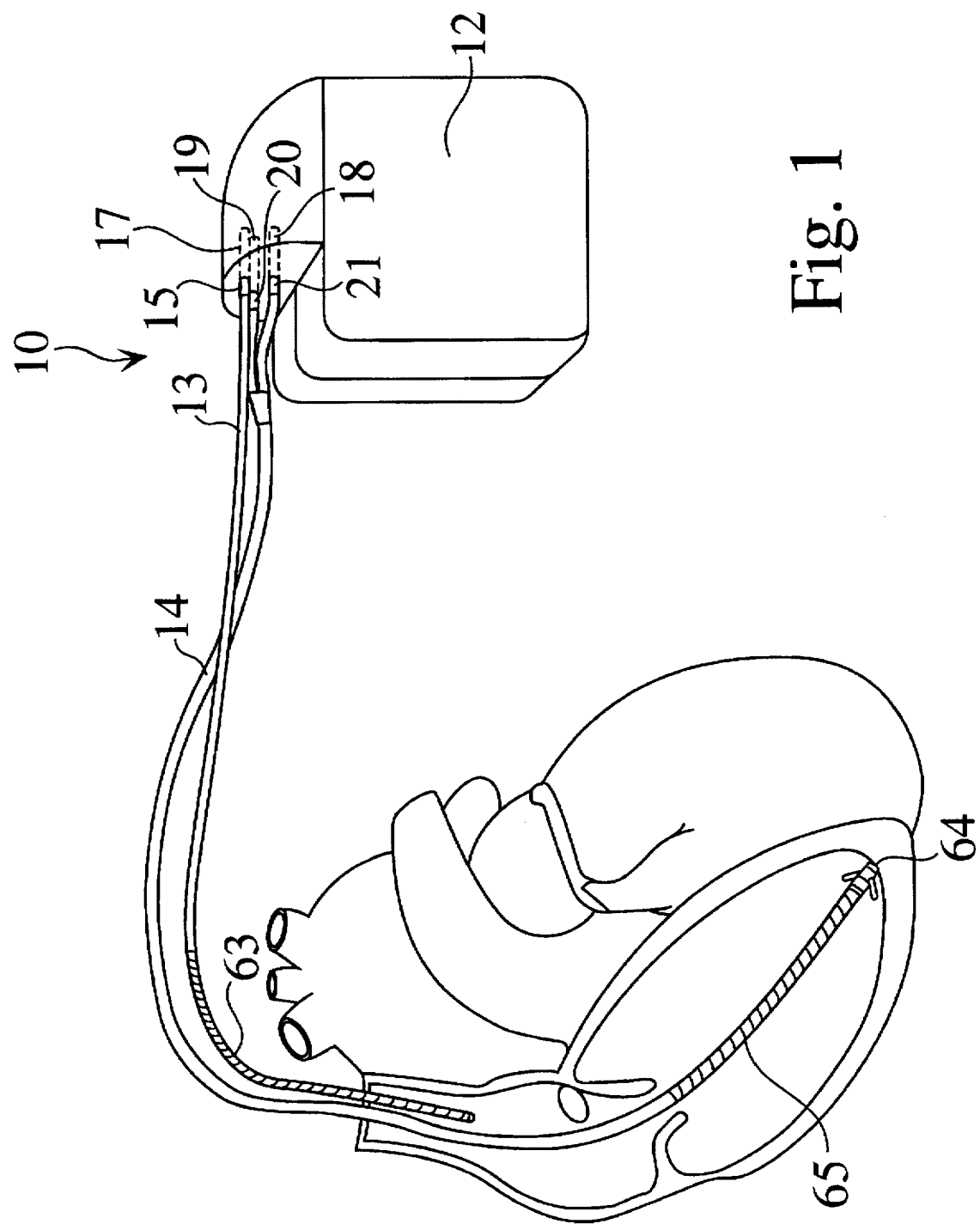
FIG. 1 illustrates an implanted defibrillator system.

FIG. 1 illustrates a pacing and/or defibrillator system 10, consisting of a pulse generator 12 and leads 13 and 14, according to the present invention. Pulse generator 12 includes a power supply and electronic circuits. Leads 13 and 14 electrically connect pulse generator 12 to the patient's heart. Lead 13 has a defibrillation electrode 63 located within the superior vena cava; lead 14 has a defibrillation electrode 65 and a distal pacing electrode 64 located within the right ventricle. Lead 13 includes lead connector 15, lead 14 is bifurcated at its proximal end and includes lead connectors 20 and 21, and pulse generator 12 includes connector cavities 17, 18, and 19.

Figure 2:
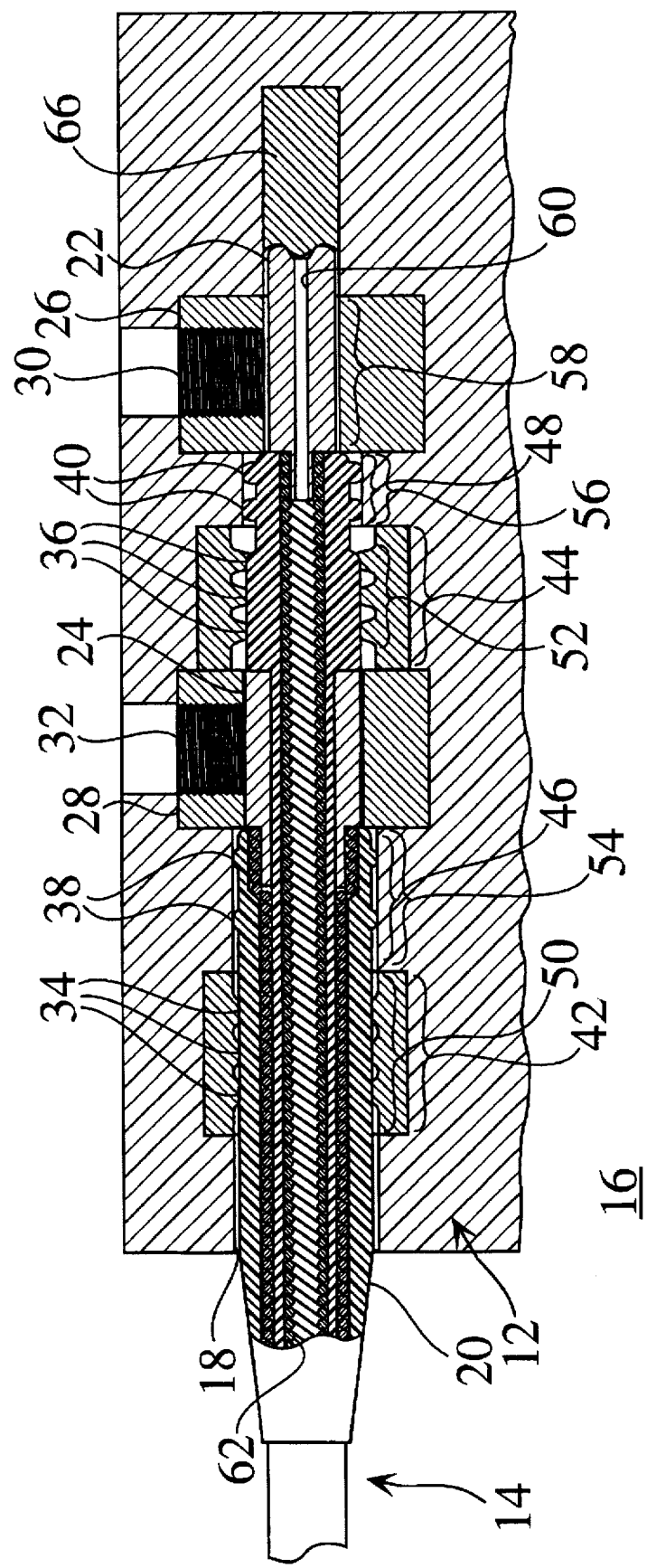
FIG. 2 is a cross sectional view of a connector assembly including the lumen sealing device of the present invention having a disk shape with a flat sealing surface.

FIG. 2 is a cross sectional view of connector cavity 18 and lead connector 20, which together make up a connector assembly 16. Connector assembly 16 provides electrical and mechanical connection of lead 14 to pulse generator 12 by inserting lead connector 20 into connector cavity 18. Lead connector 20 includes lead connector pin 22 and lead connector ring 24. Connector cavity 18 includes two connector contacts 26 and 28, which provide the current-carrying interfaces between the connector cavity 18 and the lead connector 20. These contacts are shown here as connector block/setscrew assemblies. Connector contact 26 has a setscrew 30 for contacting lead connector pin 22, and connector contact 28 has a ring setscrew 32 for contacting lead connector ring 24. For all embodiments of the invention, setscrews may be provided already located in setscrew blocks, but not tightened. Alternatively, the setscrews may be provided separately, either in the defibrillator package or as an accessory, to be inserted during implant. In addition, various methods known in the art may be used to seal the setscrew cavity from fluid ingress, such as cap screws, resealable membranes, or medical adhesive applied over the setscrew. Electrical and mechanical contact between the lead connectors and circuitry of the pulse generator 12 may be provided by other connector contacts known in the art such as are described in U.S. Pat. Nos. 4,540,236 and 4,784,141 to Peers-Trevarton, U.S. Pat. No. 5,069,209 to Posin, and in U.S. patent application Ser. No. 08/168,889 to Julian, now U.S. Pat. No. 5,489,225, entitled Electrical Terminal with a Collet Grip, all of which are incorporated herein by reference. As another alternative, connector contact 28 may include a garter spring.

Sealing mechanisms, or sealing rings, 34, 36, 38, and 40 are circumferential barriers intended to maintain the electrical insulation between electrically isolated parts of the connector assembly 16, and may be located in sealing mechanism zones 42, 44, 46, and 48 on the lead connector 20 and the connector cavity 18. The sealing rings 38 and 40 are located in sealing mechanism zones 46 and 48 of lead connector 20 such that they bear on the seal zones 54 and 56 of connector cavity 18. The sealing rings 34 and 36 are located in sealing mechanism zones 42 and 44 of connector cavity 18 such that they bear on the seal zones 50 and 52 of lead connector 20. FIG. 2 shows sealing rings in all standard sealing mechanism zones, bearing on all seal zones (also called seal areas) as defined in ISO 5841-3, ISO 11318, and the Voluntary Standard VS●1, which are incorporated herein by reference. Zones on the lead connector are located distal of the lead connector pin; zones in the connector cavity are located distal of the lead connector pin contact zone 58. It should be understood that most manufacturers supply only one set of sealing rings between electrically isolated parts of the connector assembly; that is, sealing rings are usually located either on the lead connector or on the connector cavity, but not both. In the case of a bipolar connector, such as shown in FIG. 1, two sets of sealing rings are typically located on the lead in zones 46 and 48. Unipolar connectors are typically supplied with only one set of sealing rings, located distal of the connector pin.

Lead 14 has a lumen 60 extending from the open end of lead connector pin 22, through the conductor 62, and stopping at the distal pacing electrode. A lumen sealing device 66 which is the subject of the present invention is provided in the connector cavity 18 proximal of the lead connector pin contact zone 58. This sealing device 66 is shaped like a thick cylindrical disk in FIG. 2, although many shapes, thicknesses, materials, and constructions of the inventive seal are possible. When lead connector 20 is fully inserted into connector cavity 18, the open end of lead connector pin 22 presses against sealing device 66, thereby sealing the lead lumen from fluids. Sealing device 66 is shown deforming against lead connector pin 22 which increases the contact surface area and creates a more effective seal. Sealing device 66 is preferably of a material that will not have any permanent set properties, exhibit cold flow behavior (creep), or long-term shrinkage that would allow leakage. Preferably, the material is puncture resistant, abrasion resistant, and inert to any of the fluids with which it could come into contact, including saline, silicone lubricants, and blood. One advantage gained by having the seal located within the cavity is that the problem of a surgeon accidentally damaging it is minimized.

Because the sealing device, or gasket, does not contact the blood except in the case of a primary fluid block failure, a variety of materials can be used to make the gasket. These materials are primarily elastomeric, and can be similar to those used in conventional gasket or o-ring applications. These include, but are not limited to, the following classes of elastomers and rubbers: acrylonitrile butadiene, highly saturated nitrile, fluorocarbon (Viton, trademark of Dow Corning Corp.), ethylene/propylene/diene terpolymers, styrene butadiene, chloroprene, isobutylene/isoprene (butyl), silicone, fluorosilicone, polyacrylate, ethylene acrylic, chlorosulfonated polyethylene, chloropolyethylene, epichlorohydrin, natural or synthetic polyisoprene, polyurethanes, polyvinyl chlorides, natural rubber (latex), and polybutadiene.

FIG. 3 illustrates another embodiment of the lumen sealing device 66 having a convex, or hemispherical, or "hump", shape residing within connector cavity 18, proximal of the lead connector pin contact zone 58.

FIG. 4 illustrates another embodiment of the lumen sealing device 66 having a spherical shape, residing within connector cavity 18, proximal of the lead connector pin contact zone 58.

FIG. 5 illustrates yet another embodiment of the lumen sealing device 66, shown here as comprising a disk portion 65 and sealing ridges 68, both residing within connector cavity 18 proximal of the lead connector pin contact zone 58, and therefore, also proximal of setscrew 30. Upon complete insertion of a lead connector into cavity 18, the sealing ridges 68 and disk 65 bear on the lead connector pin, preventing body fluids from any point distal of the ridges and disk from entering the lead lumen.

Figure 6A:
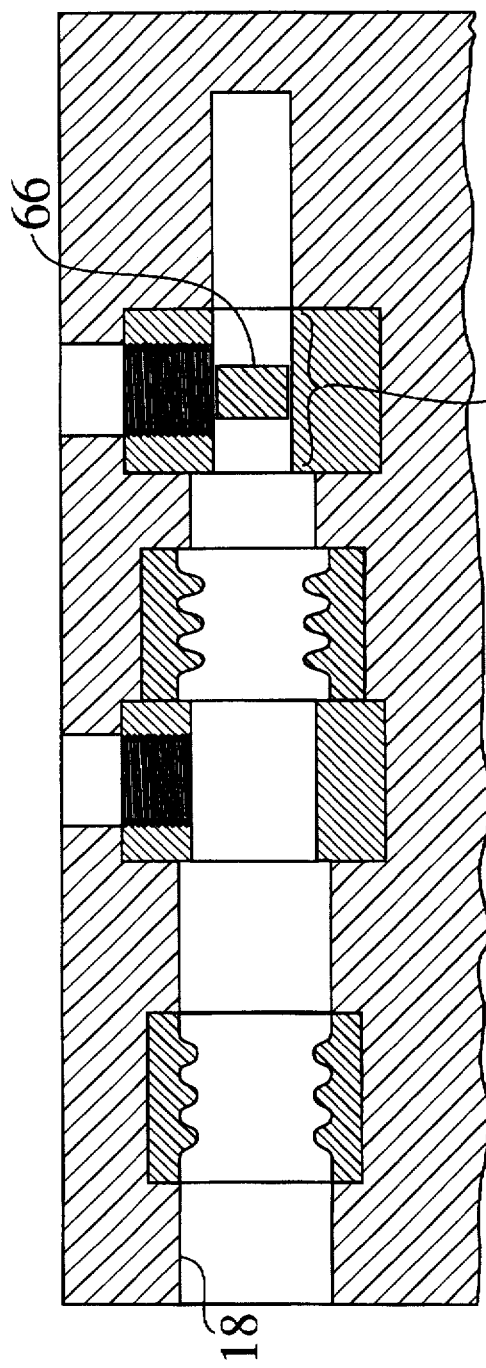
FIGS. 6A and 6B illustrate another embodiment of the lumen sealing device in the form of a pushable plug.
Figure 6B:
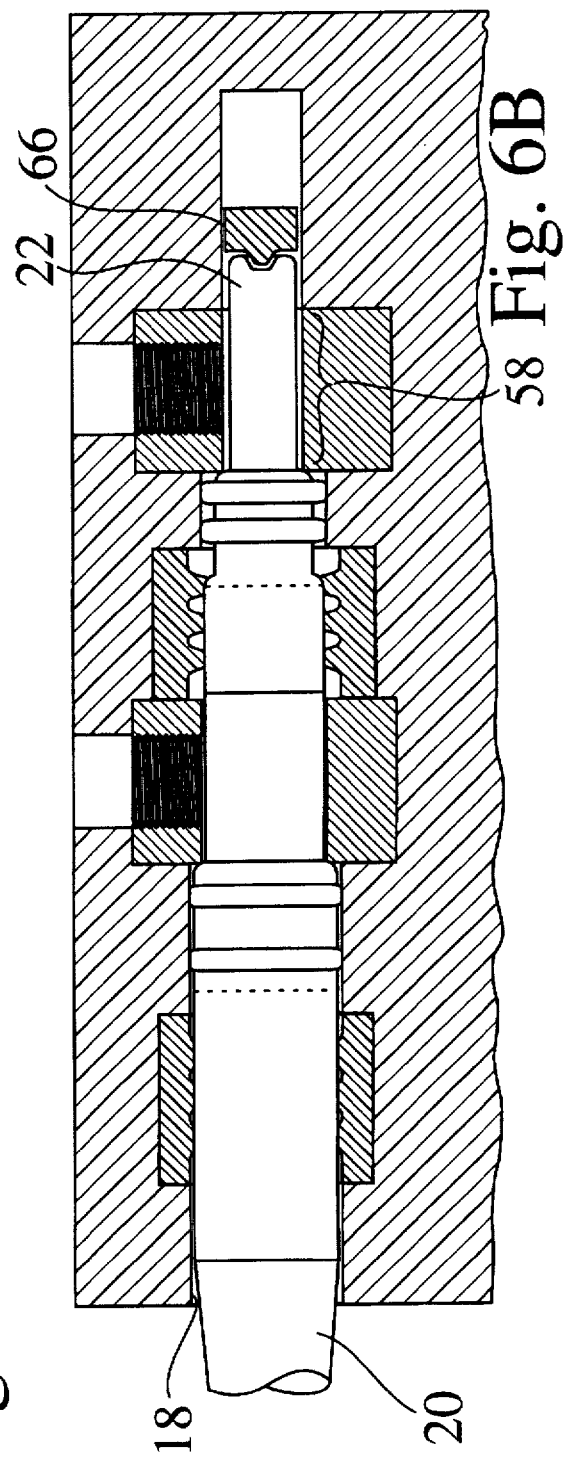

FIGS. 6A and 6B illustrate another embodiment of the lumen sealing device 66 in the form of a pushable plug. In FIG. 6A, the plug resides within connector cavity 18, at a location where a fully inserted lead connector pin would at least partially lie. In this case, the location is shown to be in the lead connector pin contact zone 58. Alternatively, plug 66 may be located proximal of the lead connector pin contact zone 58. In either case, plug 66 is not touching the proximal end of connector cavity 18. In FIG. 6B, lead connector 20 has been inserted into connector cavity 18, pushing lead connector pin 22 against plug 66, thereby pushing plug 66 deeper into connector cavity 18. As shown in FIG. 6B, there is still space between plug 66 and the end of connector cavity 18; in that case, plug 66 exerts a force on lead connector pin 22, due to friction between plug 66 and connector cavity 18. Alternatively, plug 66 may be forced up against the end of connector cavity 18.

FIGS. 7A and 7B illustrate yet another embodiment of the lumen sealing device in the form of a pushable plug 67 and a spring 70. A hump-shaped plug is shown, but the plug may be disk-shaped or spherical, or any other appropriate shape. Spring 70 may be insert molded into plug 67, or may be a separate component. A supporting piece 69 may be insert molded or assembled into lumen sealing device 66 between plug 67 and spring 70. In FIG. 7A, plug 67 resides within connector cavity 18, at a location where a fully inserted lead connector pin would at least partially lie. In this case, the location is shown to be proximal of the lead connector pin contact zone 58. Spring 70 resides between plug 67 and the end of connector cavity 18. In FIG. 7B, lead connector 20 has been inserted into connector cavity 18, pushing lead connector pin 22 against plug 67, thereby compressing spring 70 and pushing plug 67 deeper into connector cavity 18. An advantage of using a spring is that the plug can be returned to its initial position adjacent the connector block. This permits repeated lead insertion and removal to different depths without affecting effectiveness of the seal. Also, a compressible spring allows the sealing surface to travel with the end of the pin over longer distances than most compressible bulk materials.

FIG. 8 illustrates a composite lumen sealing device 66. A first material 72 forms the bulk of lumen sealing device 66, and a second material 74 forms an interface between first material 72 and the end of the lead connector pin 22. The bulk material 72 acts as the spring material of FIG. 7, having a higher elastic modulus than interface material 74. Therefore, interface material 74 deforms more readily than bulk material 72, conforming to the shape of lead connector pin 22 and forming a good seal.

FIG. 9 illustrates a lumen sealing device 66 having a bellows portion 78 which acts as the spring of FIG. 7.

Figure 10:
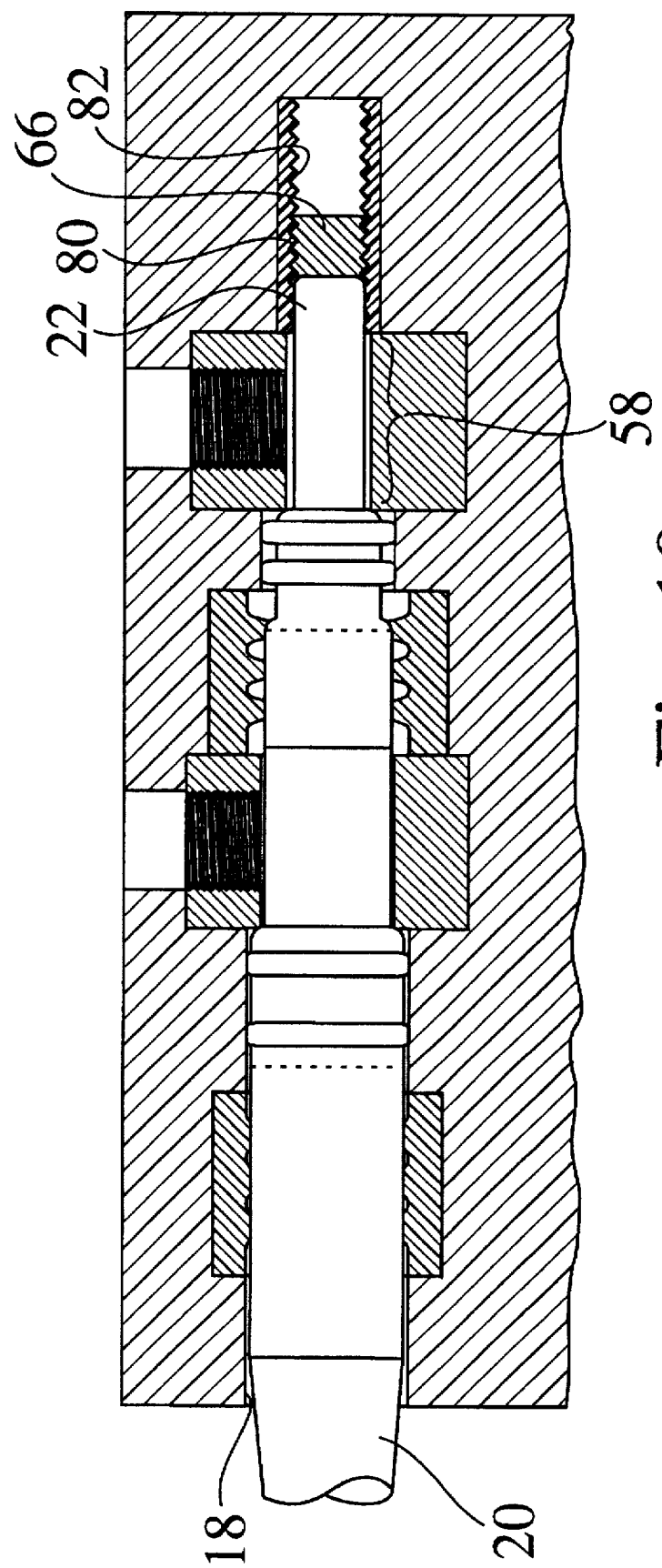
FIG. 10 illustrates a lumen sealing device in the form of a pushable plug, having indents that ratchet against connector cavity indents as the plug is pushed in by the lead connector pin.

FIG. 10 illustrates a lumen sealing device 66 in the form of a pushable plug, similar to that of 7A and 7B. The plug and connector cavity 18 have matched indents 80 and 82 that ratchet as the plug is pushed in by lead connector pin 22. Preferably, the connector cavity material forming connector cavity indents 82 is harder than the plug material forming the plug indents 80. Many shapes for the indents are possible, such as triangular, square with rounded corners, or sinusoidal. The profile of the plug is preferably the same as the profile of the connector cavity.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A medical device for use with an implantable lead comprising:

a connector cavity having an entrance end and a proximal end and adapted to receive a lead connector pin of said lead, said pin having an open end; and a gasket located within said connector cavity and adapted to contact and seal the open end of the lead connector pin against fluid intrusion when the lead connector pin is residing within said connector cavity, wherein said gasket is slidable within said connector cavity and is located spaced apart from said proximal end prior to insertion of said lead connector pin in said connector cavity.

2. The medical device of claim 1 wherein said gasket is frictionally engaged with said connector cavity.

3. The medical device of claim 1 wherein said gasket includes indents and wherein said connector cavity includes indents and wherein said gasket ratchets against said connector cavity by means of said gasket indents and said connector cavity indents during insertion of a lead connector into said connector cavity.

4. A medical device for use with an implantable lead comprising:

a connector cavity having an entrance end and a proximal end and adapted to receive a lead connector pin of said lead, said pin having an open end; and a gasket located within said connector cavity and adapted to contact and seal the open end of the lead connector pin against fluid intrusion when the lead connector pin is residing within said connector cavity, and further including a compression spring located between said gasket and said proximal end.

5. A medical device for use with an implantable lead comprising:

a connector cavity having an entrance end and a proximal end and adapted to receive a lead connector pin of said lead, said pin having an open end; and a gasket located within said connector cavity and adapted to contact and seal the open end of the lead connector pin against fluid intrusion when the lead connector pin is residing within said connector cavity, and further including a spring insert molded into said gasket.

6. A medical device for use with an implantable lead comprising:

a connector cavity having an entrance end and a proximal end and adapted to receive a lead connector pin of said lead, said pin having an open end; and a gasket located within said connector cavity and adapted to contact and seal the open end of the lead connector pin against fluid intrusion when the lead connector pin is residing within said connector cavity, wherein said gasket includes a bellows portion.

7. An implantable defibrillator system comprising:

a pulse generator having a connector cavity having an entrance end, a proximal end, and a lead connector pin contact zone located between said entrance end and said proximal end, and having an elastomeric sealing device located between said lead connector pin contact zone and said proximal end; and a lead having a lead connector including a lead connector pin having an open end, said lead connector residing within said connector cavity wherein said sealing device comprises a plug in contact with said lead connector pin open end, thereby sealing said lead connector pin open end against fluid intrusion.

8. The implantable defibrillator system of claim 7, wherein said sealing device further includes circumferential sealing rings located within said connector cavity between said lead connector pin contact zone and said gasket.

* * * * *